United States Patent [19]

Wallace et al.

[11] Patent Number: 5,238,714
[45] Date of Patent: Aug. 24, 1993

[54] EFFICIENT MICROCAPSULE PREPARATION AND METHOD OF USE

[75] Inventors: Sidney Wallace, Houston; David Yang, Sugarland; Michael Wallace, Houston, all of Tex.

[73] Assignee: Board of Regents, The University of Texas System, Austin, Tex.

[21] Appl. No.: 592,020

[22] Filed: Oct. 2, 1990

[51] Int. Cl.$^5$ .......................... B01J 13/12; A61K 9/52
[52] U.S. Cl. ............................ 427/213.36; 427/213.3; 424/497; 424/426; 424/9; 424/5
[58] Field of Search .................... 427/213.3, 213.36; 264/4.6

[56] References Cited

U.S. PATENT DOCUMENTS

| | | | |
|---|---|---|---|
| 3,891,570 | 6/1975 | Fukushima et al. | 427/213.36 |
| 4,272,398 | 6/1981 | Jaffe | 427/213.31 |
| 4,479,911 | 10/1984 | Fong | 264/4.6 |
| 4,492,720 | 1/1985 | Mosier | 427/213.3 |
| 4,931,362 | 6/1990 | Zsifkovits et al. | 428/402.22 |
| 4,933,105 | 6/1990 | Fong | 427/213.36 X |
| 4,994,281 | 2/1991 | Muranishi et al. | 424/497 |
| 5,100,669 | 3/1992 | Hyon et al. | 427/213.36 X |

FOREIGN PATENT DOCUMENTS 0302582 8/1989 European Pat. Off. .
0326722 8/1989 European Pat. Off. .

OTHER PUBLICATIONS

Wright et al., "Microcapsules for arterial chemoembolization: appearance and in vitro drug release characteristics", *J. Microencapsulation*, vol. 5, No. 1, pp. 13–20, 1988.

Wright et al., "Regional Isolation–Perfusion: An Experimental Percutaneous Approach Tested and Compared with Arterial Occlusion–Infusion", Cardiovasc. Intervent. Radiol., vol. 7, pp. 294–298.

Bechtel et al., "An Experimental Evaluation of Microcapsules for Arterial Chemoembolization", *Radiology*, vol. 161, pp. 601–604, 1986.

Kawashima et al., "Drug Release Properties of the Microcapsules of Adriamycin Hydrochloride With Ethylcellulose Prepared by a Phase Separation Technique", *Drug Development and Industrial Pharmacy*, vol. 10, No. 3, pp. 467–479, 1984.

Benita et al., "Characterization of Drug-Loaded Poly(d,l-lactide) Microspheres", *J. of Pharm. Sci.*, vol. 73, No. 12, pp. 1721–1734, Dec. 1984.

Tice and Gilley, "Preparation of Injectable Controlled-Release Microcapsules by a Solvent-Evaporation Process", *J. of Controlled Release*, vol. 2, pp. 343–352, 1985.

Smith and Hunneyball, "Evaluation of poly(lactic acid) as a biodegradable drug delivery system for parenteral administration", *Intl. J. of Pharm.*, vol. 30, pp. 215–220, 1986.

Sections 1.4–1.6, 3.1 and 3.4 of Book by Bruning and Kintz.

Dialog Search–Abstracts of references relating to microencapsulation and sustained drug delivery.

Dialog Search–Abstracts of references relating to microencapsulation of therapeutic agents.

*Primary Examiner*—Robert L. Stoll
*Assistant Examiner*—John M. Covert
*Attorney, Agent, or Firm*—Arnold, White & Durkee

[57] ABSTRACT

The present invention relates to a method of preparing microcapsules suitable for encapsulation of therapeutic and diagnostic agents. The capsular coats are prepared from biodegradable polymers. In a particular aspect of the invention, surface charge of the polymeric material is altered by conjugation of an amino acid ester to the polymer, providing targeting to specific tissue cells. Encapsulation of hydrophilic radiodiagnostic agents in 1 μm capsules provides improved opacification. Encapsulation of cytotoxic agents in 100 μm capsules is useful in chemoembolization procedures.

13 Claims, 20 Drawing Sheets

PLA MICROCAPSULES (10μ) LOADED
WITH MEGLUMINE DIATRIZOATE, 20,000X

EFFICIENT MICROCAPSULE PREPARATION AND METHOD OF USE

BACKGROUND OF THE INVENTION

1. Field of the Invention

The invention relates generally to a reproducible, efficient method of preparing nonaggregated microcapsules suitable for encapsulation of diagnostic and therapeutic agents. The invention also relates to methods of use for encapsulated diagnostic and therapeutic agents and in particular aspects to the use of amino acid conjugated polymers as microencapsulation materials. Conjugated amino acid ester microencapsulated agents have particular potential for drug targeting.

| LIST OF ABBREVIATIONS | |
|---|---|
| PLA | poly-(D,L)-lactic acid |
| PCL | polycaprolactone |
| PCLD | polycaprolactone diol |
| 5-FU | 5-fluorouracil |
| TX | Tamoxifen |
| EHEC | ethylhydroxyethyl cellulose |
| CDDP | cisdiamminedichloroplatinum, (cisplatin) |
| MAA | macroaggregated albumin |
| DTPA | diethyltriaminepenta-acetic acid |

2. Description of Related Art

Microencapsulation is a well-studied art. It is basically the use of a matrix or encapsulating material to enclose gases, liquids or solids into particles of relatively small size (0.5–500 $\mu$m). The matrix is capsular material selected according to the intended use of the microcapsules.

Physical properties of encapsulated chemical entities may be modified because of the encapsulation. Other effects of encapsulation include dispersion of one substance within another, stabilization of emulsions and alteration of solubility rate. One of the most useful properties of encapsulated therapeutic materials is controlled release (1,2).

Microcapsules have been prepared by many methods, including coacervation, interfacial polymerization, mechanical methods, polymer dispersion and matrix encapsulation. Sustained release microcapsules have been prepared from ethylcellulose (3) and poly-(D,L)-lactide (4). There is voluminous literature on the preparation and use of encapsulating polymers designed for sustained drug release (5,6).

Although many preparations of microencapsulated compounds have been reported, few describe microparticles in the size range below 10 $\mu$m. Particles of 1–250 $\mu$m are typically prepared by a solvent evaporation technique (7) while sizes from 1–10 $\mu$m have been made by emulsion deposition (8). One method using solvent evaporation claims to provide a range of sizes from 0.5–250 $\mu$m (9). Nevertheless, none of these methods appears to provide a homogeneous preparation of single-particle, nonaggregated microcapsules. Typical of these preparations is a claim to aggregate having an overall size of about 177 to 395 $\mu$m with 5–162 $\mu$m particles making up the aggregates (10). This technique requires sieving to remove larger agglomerates, leaving behind a wide range of particle sizes which, although composed of small spheres, are nevertheless in aggregated form.

Discrete microprills, polymeric particles in which a drug (for example, Mellarib ™) is uniformly dispersed, have been disclosed (11). Although the microprills were reported to be nonaggregated, the average size range was 10–50 $\mu$m.

Lack of particle size homogeneity may cause severe problems in quality control and in clinical use. For example, in chemoembolization studies, the particle diameter is fairly critical in that only a limited range of sizes will lodge in a target area (12). If too large, damage to larger vessels may occur, while if too small, the particles pass through and drug is not released at the targeted site. Thus a homogeneous particle preparation is important.

Despite the proliferation of microencapsulation methods, there is a particular need for simple and efficient methods of producing homogeneous preparations of microencapsulated agents for clinical treatment and diagnosis, most particularly in small, nonaggregated particles ranging from 0.5 to 500 $\mu$m. A method of preparing encapsulated therapeutic agents in 1 $\mu$m and 100 $\mu$m particles would provide more effective agents, particularly for diagnostic imaging and chemoembolization.

Bioimaging agents microencapsulated in 1 $\mu$m particles would provide an ideal size particle for bioimaging studies, particularly if combined with capsular material selected to concentrate in the organ of interest. Additionally, the use of microencapsulation materials capable of targeting particular areas in vivo would enable improvements in biodistribution imaging studies as well as in drug delivery to specific organs.

SUMMARY OF THE INVENTION

The present invention is a highly efficient, reproducible method of obtaining homogeneous nonaggregated preparations of polymeric microcapsules in which therapeutic or diagnostic agents may be encapsulated. The invention also includes microcapsules prepared from polymers conjugated to an amino acid, enabling improved targeting of drug-laden microcapsules to a particular target organ or cell. The invention illustrates two important size ranges, 1 and 100 $\mu$m, of polymeric particles useful in clinical studies and in which imaging or therapeutic agents may be efficiently encapsulated.

An important aspect of the invention is the preparation of homogenous nonaggregated microcapsules having a diameter of approximately 1 $\mu$m. These microcapsules are prepared by combining solution which may contain a drug or therapeutic agent, a nontoxic emulsifier and polymer dissolved in convenient solvent, and then vigorously agitating the mixture. Agitation is performed for a period of time sufficient for the development of microcapsules having a mean diameter below 5 $\mu$m. The formation of the microcapsules is monitored periodically, after which the organic solvent is removed and the microcapsules collected.

The nontoxic emulsifier may be selected from several commonly used emulsifiers, for example Tween-80, polyvinyl alcohol, sodium laurylsulfate, Span 20, Lubrol, Triton ™ X-100, or cetylpyridinium chloride. Thus a wide variety of emulsifiers may be suitable, including anionic, cationic, and non-ionic types.

Likewise, a wide variety of materials, including several types of polymers, may be used for the preparation of the capsules. Microcapsules particularly useful for clinical or therapeutic purposes release their contents by erosion, degradation or diffusion. Polymers suitable for this purpose include poly-(D,L)-lactic acid, ethylhydroxyethyl cellulose, polycaprolactone, polycaprolactone diol, polylysine, polyglycolic acid, and polymaleic acid. This is not to say that the polymer used for medical treatment must be biodegradable. For example, relatively permanent implantable drug-containing polymers (e.g., hydrogels) might be used for long-term sustained release in certain applications.

Generally speaking, the emulsifier is soluble in water, while the polymer, insoluble in water, is dissolved in an appropriate organic solvent. Immiscible or miscible organic solvents may be used, depending on the nature of the polymer. For example, the polymer may be dissolved in acetone, water, or insoluble solvents such as ethyl acetate, chloroform, carbon tetrachloride and methylene chloride.

An important step in the preparation of nonaggregated microcapsules less than 5 $\mu$m in diameter is the vigorous agitation of the mixture containing polymer, emulsifier and, when desired, a diagnostic or therapeutic agent. Agitation may be carried out by stirring, sonication, or a combination of agitation methods. If stirring alone is used, a speed of approximately 1500 rpms is preferred. If both stirring and sonication are used, sonication at approximately 20 Khz and stirring at 500 rpms are preferred settings. Sonication and stirring are most preferably used simultaneously. Agitation is continued for a period of time sufficient to form individual microcapsules with an average size less than 5 $\mu$m. The time required to form 1 $\mu$m microcapsules is approximately 90-1100 minutes; however, shorter or longer periods of time may be required depending on the conditions, the organic solvent used, the volume and concentration of starting material as well as pH and temperature. It is important to monitor microcapsule formation by periodically examining size and shape of the microcapsules as they form in solution. Any method that detects size and shape of the capsules may be used, for example, removal of a drop of the solution and inspection under a light microscope at a magnification of approximately 600 fold.

After the microcapsules have formed, the organic solvent is removed from the mixture. A convenient method, particularly for lower boiling organic solvents, is to stir the reaction mixture at relatively slow rpms, for example about 350 rpm, for a period of several hours until the solvent is completely evaporated. The length of time depends on the type and volume of solvent in addition to other factors related to physical properties. For example, the solvent acetone require about six hours for complete evaporation. Other solvents with lower vapor pressure/higher boiling points may require longer periods of time. Evaporation, in this process, occurs at room temperature, but higher temperatures may be applied when different solvents are used. Monitoring of capsule size and shape continues to be important throughout the evaporation phase to assure that aggregation does not occur.

The microcapsules are collected, after complete evaporation of the organic solvent, preferably by filtration, for example, by filtration through a nylon mesh or other suitable filter that allows smaller particles to pass through while retaining the larger particles. The resulting suspension containing 1 $\mu$m microcapsules may then be further processed to isolate and store or use the particles. This is conveniently accomplished by centrifuging the suspension after which any residual organic solvent or emulsifier can be removed by washing either with water or sterile saline. The aqueous layer may then be decanted and the microcapsules resuspended in a liquid for storage or for therapeutic use. When used therapeutically, phosphate buffered saline, pH 7.4 is a most preferred resuspension medium. This method has provided a high yield (99%) of nonaggregated 1 $\mu$m particles. The amount of material collected in the nylon sieve is rarely over 1%, and the microparticles prepared by this method are remarkably uniform with a narrow size distribution ranging from 0.5 to 5.0 $\mu$m with the highest percentage being approximately 1.0 $\mu$m.

These microcapsules can be used to enhance or modify properties of diagnostic or therapeutic agents by virtue of the encapsulation. For example, in order to alter biodistribution properties, an ionic radiographic contrast agent may be encapsulated in a nonionic coat using this microencapsulation process. In the first step of preparing an encapsulated drug, the diagnostic or therapeutic agent is added to a mixture containing an aqueous solution, an emulsifier, and a polymer dissolved in solvent. During microparticle formation, the drug is encapsulated. The yield depends on the material being encapsulated. For example, 1 $\mu$m and 100 $\mu$m capsules of meglumine diatrizoate have relatively high efficiencies of encapsulation of 66% and 46% by weight respectively. Therapeutic agents (cisplatin, 5-fluorouracil and Tamoxifen) and diagnostic agents (Ethiodol, Iohexol, diatrizoate and Hexabrix) have also been incorporated into 100 $\mu$m capsules. Encapsulation is not intended to be limited to these particular drugs and it is envisioned that most therapeutic and diagnostic agents, whether water soluble or insoluble, could be encapsulated by this simple method.

Those skilled in the art will appreciate that this method of encapsulation of therapeutic or diagnostic agents will result in an entrapment of the material, which will be released from the microcapsule at different rates depending on the relative amount of polymer to amount of drug encapsulated. Other factors affecting the rate of release are the chemistry of the compound being encapsulated, the environment into which the microcapsule is being placed, temperature of the environment and the nature or chemical composition of the capsular material. The rate of release of drug will also be determined by the relative ratios of drug to polymer, the type of polymer, and the biodegradability of the polymer.

One $\mu$m microencapsulated imaging agents are ideal for diagnostic imaging procedures and are readily prepared by the method of the invention. First, a homogeneous nonaggregated preparation of a 1 $\mu$m microencapsulated imaging agent is prepared as previously described. The material may be any standard imaging agent, for example, an iodinated compound such as meglumine diatrizoate. The microencapsulated imaging agent can then be administered to an animal or human, preferably by intra-arterial or intravenous injection. The imaging agent is then detected by appropriate means such as computed tomography or intravenous urography.

Normally, drugs or other agents administered to an animal or human will initially disperse through the body before concentrating in the liver, spleen, kidneys and urinary bladder prior to elimination. It was a surprising discovery that amino acid ester conjugation to polymers affected the character of the capsule causing distribution and uptake of the encapsulated imaging material in an animal to be altered. In a particular example, phenylalanine-conjugated polylactic acid was used to encapsulate meglumine diatrizoate. The animal injected with phenylalanine ester-conjugated encapsulated diatrizoate showed faster liver uptake than animals injected with nonconjugated polymer capsules. In the former case, imaging was possible as early as sixty minutes after injection. Two hours post injection, the non-conjugated microencapsulated material showed both liver and kidney uptake as well as presence in the systemic circulation. The conjugated microencapsulated material was concentrated mainly in the liver and showed little in the general circulation at two hours post-injection. Both non-conjugated and amino acid-conjugated poly-(D,L)-lactide microencapsulated diatrizoate permitted computed tomography imaging up to three days after administration. Neither material was seen in the liver five days post-administration. In vitro mouse liver cell culture studies revealed that the conjugated microcapsules were mainly taken up by hepatocytes whereas the nonconjugated microcapsules were taken up by Kupffer cells. Other amino acids conjugated with polymeric encapsulating material also would be expected to show selective targeting of encapsulated drugs.

Although amino acid conjugated polymers were formulated using phenylalanine ester, other amino acids such as tyrosine, tryptophan, or methionine are also contemplated to be useful. A selected amino acid is most conveniently conjugated to the polymeric material via an amide bond to link phenylalanine with poly-lactic acid. This may be done through a variety of carbodiimide coupling procedures well known to those experienced in the art, for example, by reacting with dicyclohexylcarbodiimide in the presence of hydroxysuccinimide. Covalent bonds need not be limited to linkages involving the primary amine of the amino acid but might, for example, utilize a sulfur-carbon bond between a sulfhydryl-containing amino acid and the polymer. Furthermore, depending on the nature of the functional groups on the polymer, other types of linkages could be formed, for example, ether linkages. The use of other conjugates is also envisioned. For example, sugars, amino acids or derivatives of these compounds could also be used to surface-modify a microcapsule polymer.

The general method used for the preparation of 1 $\mu$m microcapsules can also be used to make microcapsules of somewhat larger sizes, for example, 100 $\mu$m. Non-aggregated microcapsules having a mean diameter of 100 $\mu$m can be prepared by combining a polymer in a solvent with a solution of a nontoxic emulsifier. The mixture is emulsified by stirring at low speed, approximately 350 rpm, while monitoring microcapsule formation. The solvent is the evaporated and the microcapsules collected.

One difference between this procedure for preparing 100 $\mu$m microcapsules and preparing 1 $\mu$m microcapsules is stirring the mixture of the polymer and the emulsifier at a relatively lower speed when the larger particles are desired. The stirring speed is approximately 350-400 rpm. During the stirring process, the size and shape of the particles in the mixture are monitored, for example, by using a light microscope at approximately 125× magnification. After the desired size range of microcapsules has formed, the organic solvent is removed, preferably by evaporation and simultaneous stirring at room temperature. After collection and drying, the microcapsules are preferably sized. This may be accomplished by passing the particles through various sized filters, for example, first 600 $\mu$m mesh, then 600-500 $\mu$m mesh, then 500-355 $\mu$m mesh, then 355-212 $\mu$m mesh, and finally 106 $\mu$m mesh. The sieved particles yield a mixture containing size ranges of approximately 106-212 $\mu$m. Use of these mesh sizes is for illustration purposes only and, of course, any series of that same general size mesh could be used. In the final step the 106-212 $\mu$m particle mixture is sieved through a 106 $\mu$m mesh sieve and the particles that pass through the sieve are discarded. This provides a relatively uniform preparation. Using this method, consistently reproducible yields of approximately 70% of particle sizes in the size range of 100-200 $\mu$m have been obtained.

In preparing 100 $\mu$m diameter particles, any of a number of polymers may be used, including biodegradable polymers such as poly-(D,L)-lactic acid, ethylhydroxyethyl cellulose, polycaprolactone, polycaprolactone diol, polylysine, polyglycolic acid or polymaleic acid.

In the initial step of 100 $\mu$m microcapsule preparation, the polymer is first dissolved in an organic solvent then mixed with emulsifier. The solvents may include methylene chloride, chloroform, carbon tetrachloride, or any other organic solvent in which the polymer is soluble. The emulsifier may be selected from any of a group of nonionic, cationic, or anionic emulsifiers. A nontoxic emulsifier is preferably chosen when these described microcapsule preparations are used to encapsulate therapeutic or diagnostic agents for in vivo use. The nontoxic emulsifier is preferably solubilized in saline, although water or buffers can be used. Therapeutic or diagnostic agents which are hydrophobic or hydrophilic may be microencapsulated in the 100- 200 $\mu$m particles. These compounds will slowly release from the microcapsules and the rate of release will depend on the nature of the compound encapsulated as well as the type of polymeric material used for the microcapsule.

It has been found that the 100-200 $\mu$m microcapsules are ideal for chemoembolization. When chemoembolization is desired, a drug encapsulated in a biodegradable or nondegradable polymer is prepared. The microcapsule generally has a diameter of about 100 $\mu$m which is somewhat larger than the diameter of the tumor vessels in the targeted organ. Encapsulated material is administered intra-arterially causing occlusion of the arteries. By occluding the arterial supply to neoplasms with 100 $\mu$m capsules, the ischemia results in death of the tumor cells. The rate of release will depend on the nature of the material used to prepare the microcapsules. Slow release over hours or weeks allows greater contact time between the cytotoxic agents and tumor cell in an anoxic environment which also increases capillary permeability.

Examples of microencapsulated drugs useful for chemoembolization are cisplatin, 5-fluorouracil and Tamoxifen. In one particular example, cisplatin was microencapsulated and administered into canine renal arteries. Poly-(D,L)-lactide capsules and ethylhydroxyethyl cellulose capsules, both loaded with cisplatin, exhibited sustained cisplatin release for at least several days. The resulting tissue destruction was significantly greater than that with blank capsules. These sustained-release effects should be similar for other drugs.

Surface properties of 100 $\mu$m microcapsules may be modified in the same manner as surface properties of the 1 $\mu$m microcapsules by conjugating with various amino acids or other surface-modifying materials. In the case of chemoembolization studies, surface modification would likely be important. These particles could be delivered intra-arterially to the organ of interest.

DETAILED DESCRIPTION OF PREFERRED EMBODIMENTS

The invention is a method of preparing microencapsulated therapeutic and diagnostic agents in discrete nonaggregated particles suitable for diagnostic radiologic studies and therapeutic use in humans. In particular, the method relates to preparing 1 μm particles for intravenous and intra-arterial administration as well as 100 μm particles for intra-arterial use. In another aspect of the invention, cells in the body are specifically targeted with drugs microencapsulated in polymeric material whose surface properties are modified by conjugation with an amino acid.

The following examples are intended to illustrate specific embodiments of the present invention. Those skilled in this field will recognize that modifications could be made to the disclosed methods and that other applications would remain within the scope of the present invention.

EXAMPLE 1

100 Micron Microcapsule Preparation of Microencapsulated Meglumine Diatrizoate

Meglumine diatrizoate, 2 g, was dispersed in 40 ml methylene chloride and 1 g poly-(D,L)-lactic acid added to the mixture. Encapsulation was achieved while stirring at 350 rpm in 250 ml 0.9% (w/v) saline solution containing 1.25 g polyvinyl alcohol. The pH of the solution was adjusted below 4 with 1N HCl. From time to time, formation of microcapsules was determined by examining a drop of the material at 125x magnification under a light microscope. The mixture was stirred for approximately 6 hr until the methylene chloride was completely evaporated. The microcapsules were collected by filtration and washed with distilled water (2×100 ml). The microcapsules were air dried at room temperature and then sieved through various meshes, including stepwise, 600 μm mesh, 600-500 μm mesh, 500-355 μm mesh, 355-212 μm mesh and 106 μm mesh, to give a mixture containing particles of size range 106-212 μm. The weight of the 106-212 μm particles was approximately 70% of the initial total amount of the contrast agent plus polymer. The microcapsules contained 46% (w/w) of meglumine diatrizoate.

EXAMPLE 2

1 Micron Microcapsule Preparation of Microencapsulated Meglumine Diatrizoate All the following steps were done under aseptic conditions using ultraviolet light with sterile instrumentation.

Figure 7A:
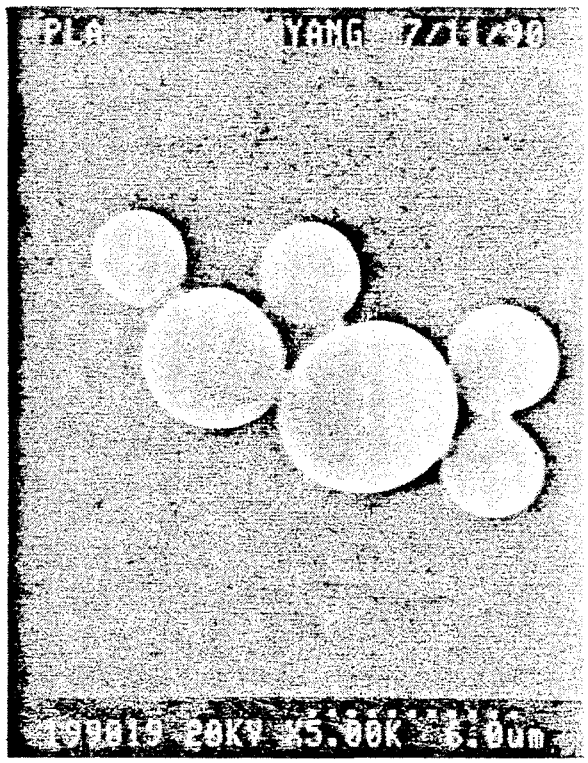
FIG. 7 is a scanning electron micrograph of 1 μm PLA microcapsules (7B) and PLA microcapsules encapsulating meglumine diatrizoate (7A) Drug to polymer ratios were 3:1.
Figure 7B:
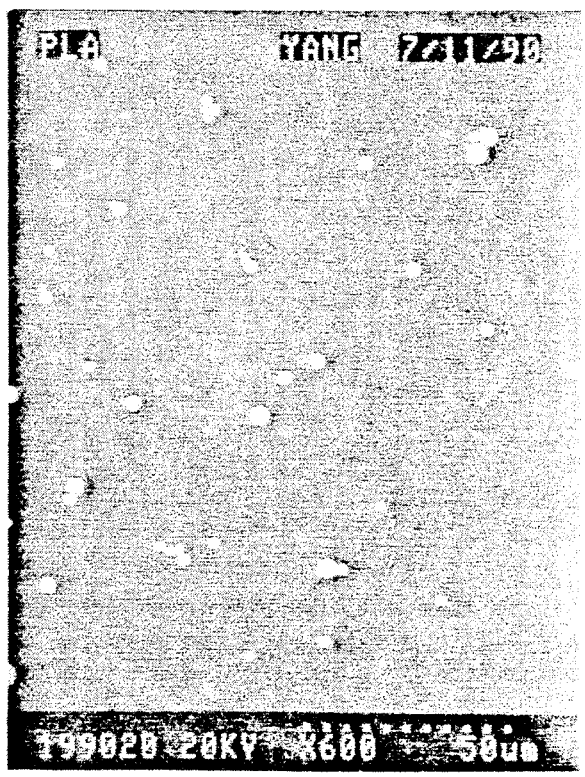
Figure 8:
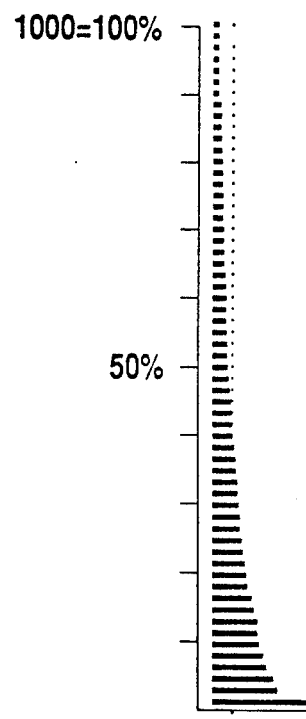
FIG. 8 is a microcapsule size distribution curve with data taken from Coulter Counter measurements. Polylactic acid microcapsules were loaded with meglumine diatrizoate.

Meglumine diatrizoate, 1.2 g (Sigma Chemical Company, St. Louis, Mo.), was dissolved in 100 ml water and then 1 ml of Tween 80 was added. The mixture was stirred at 500 rpm and the pH of the solution adjusted below 4 with 1N HCl. To this mixture was added dropwise 0.5 g poly-(D,L)-lactic acid (MW 30,000-60,000) dissolved in 10 ml acetone. The mixture was stirred at 1500 rpm or sonicated at 20 Khz for 100 min and periodically monitored under a light microscope at 600x magnification until round particles of approximately 1 μm in diameter were observed. The mixture was stirred at 1500 rpm (without sonication) or 500 rpm (with sonication) for an additional 6 hr or until the acetone was completely evaporated. The microcapsules were collected by sieving through a nylon mesh to remove a small amount of aggregated material, approximately 1%. The microcapsule suspension was centrifuged at 24,000×g and washed 3 times with saline to remove the emulsifier. The microcapsules were resuspended in sterile phosphate buffered saline. The microcapsules weighed 1.5 g (90% by total initial weight of contrast plus polymer). The microcapsules contained 66% by weight of meglumine diatrizoate. The particles were cultured and found to be sterile. Scanning electron microscopy (SEM) revealed round, uniform particles as shown in FIG. 7. The distribution of particles was determined using a Coulter counter, indicating a narrow range of 2-7 μm with 50% having a mean capsular size less than 5 μm, as indicated in FIG. 8.

EXAMPLE 3

Conjugation of Amino Acid Ester to Polylactic Acid

To a solution of 2.0 g (0.05 mmol) poly-(D,L)-lactic acid in 10 ml dimethylformamide (DMF) was added 1.2 g (5.5 mmol) of dicyclohexylcarbodiimide and 0.68 g (5.5 mmol) of N-hydroxysuccinimide. After stirring 10 min, 1.2 g (5 mmol) phenylalanine ester dissolved in 5 ml DMF was added. The mixture was stirred overnight. The solid urea was filtered. The filtrate was poured into 100 ml water and the white solid precipitated. The solid was filtered, washed with 100 ml water, air dried and weighed to obtain 2.4 g (75%) of the total chemical yield. Thin layer chromatography indicated a single spot (Rf=0.3, chloroform/methanol 9:1). The phenylalanine content in the polymer conjugate was 23% as determined by ultraviolet spectroscopy at 254 nm. Similar conditions were used to prepare microcapsules of polylactic acid conjugated with methionine, tyrosine or tryptophan ester.

EXAMPLE 4

Chemoembolization with Microencapsulated Cisplatin

Eighteen adult mongrel dogs were anesthetized with intravenous sodium pentobarbital (Nembutal; Abbott, North Chicago, Ill.), 30 mg/kg, and an intravenous drip of normal saline was initiated. Through a cutdown, a 5-F polyethylene catheter was introduced into the femoral artery, and the animal was given an intra-arterial bolus of sodium heparin (100 units/kg). The catheter was then advanced into one of the renal arteries. The ipsilateral renal vein was also catheterized via a femoral vein with a 5-F catheter to sample blood for cisplatin (CDDP), while simultaneous systemic venous blood samples were collected through an 18-gauge Cathlon TM catheter inserted in a jugular vein.

Figure 13:
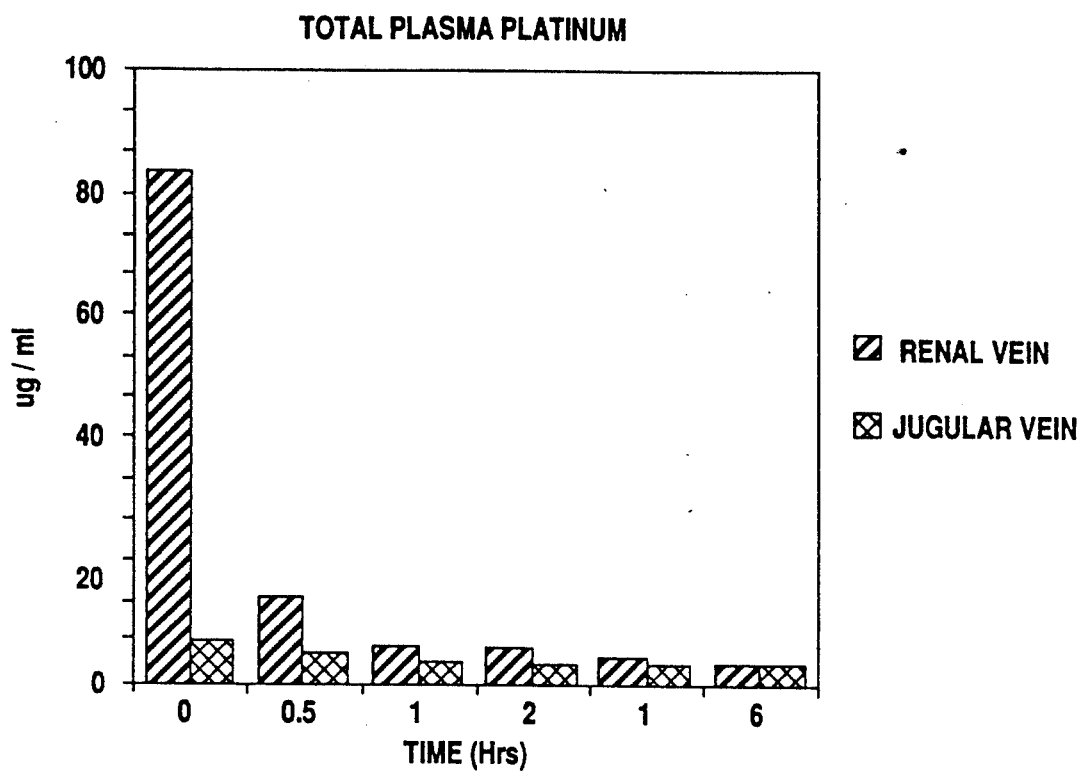
FIG. 13 shows the release of CDDP from 100 μm polylactide capsules as measured in jugular and renal vein plasma in dogs at selected times over a period of 6 hours. The drug was administered intra-arterially into the renal artery.
Figure 14:
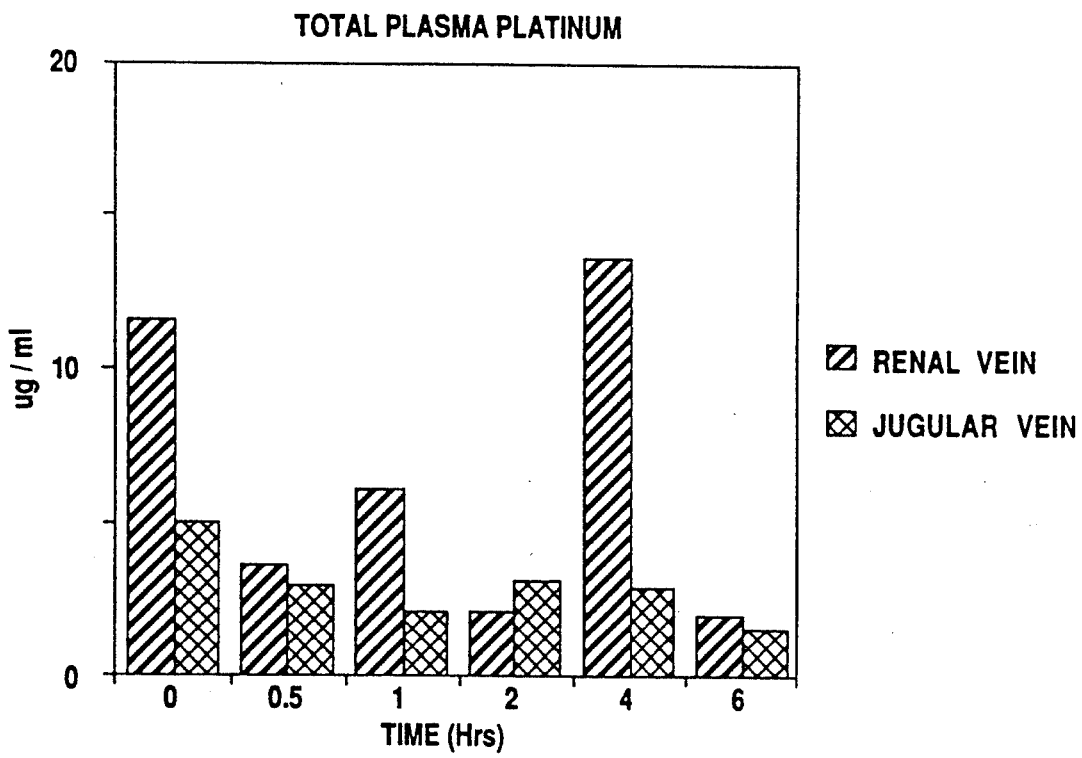
FIG. 14 shows the release of CDDP from 100 μm EHEC capsules as measured in jugular and renal vein plasma from dogs at selected times over a period of 6 hours. The drug was administered intra-arterially into the renal artery.

Microcapsules with an average size of 106 μm (range 50-350 μm) and containing cisplatin (40-43%) by weight, were formulated as described in Example 1 from lactic acid polymer and ethylhydroxyethyl cellulose polymer. The capsules, in dry form, were sterilized with ethylene oxide. The microcapsules were suspended in a 1:1 solution of radiographic contrast material. Iohexol (Omnipaque, Nycombed, Norway) and normal saline such that the final concentration was 20 mg/ml. The suspension was administered into the renal artery until stasis of flow was observed fluoroscopically. One kidney was embolized in each of three animals with each of the capsular materials containing CDDP, and one kidney from each of five dogs was occluded with each of the capsular materials without CDDP. Renal and systemic venous blood samples were collected in heparinized tubes at 30-minute intervals for 6 hours after embolization. The plasma was analyzed for CDDP using atomic absorption. Drug release curves were generated from these data. Two such curves are shown in FIGS. 13 and 14. To evaluate renal and hepatotoxicity, systemic venous blood samples were collected before and at 1, 2, 3, 4, and 6 weeks after embolization to determine blood urea nitrogen (BUN), creatinine, and serum glutamic oxaloacetic transaminase (SGPT) levels.

Renal angiography was performed with Omnipaque before and immediately after embolization, at hourly intervals up to 6 hours after embolization, and 1, 2, 4 and 6 weeks later to document the radiographic changes in the occluded kidneys. After 6 weeks, each animal was killed with an overdose of sodium pentobarbital, and a complete necropsy performed. The gross and microscopic findings in each dog were compared.

Both PLA and EHEC capsules without encapsulated drug produced embolic effects in the kidneys. The polymers loaded with cisplatin damaged kidneys significantly more than polymers alone. PLA capsules loaded with cisplatin had a greater effect on tissue than cisplatin-loaded EHEC capsules. EHEC capsules without CDDP showed slightly more degradation than PLA capsules in these studies.

In vitro drug release data were also determined by incubation of the microcapsules in phosphate buffered saline. The data is shown in Table I for release of CDDP from CDDP:PLA microcapsules.

TABLE 1

RELEASE RATE OF CDDP FROM CDDP MICROCAPSULES[1] (SIZE 100 μm)

| Incubation Time (min) | % Released |
|---|---|
| 1 | 11.6 |
| 5 | 21.3 |
| 15 | 27.4 |
| 30 | 39.5 |
| 60 | 37.7 |
| 120 | 35.0 |
| 240 | 40.4 |

[1]CDDP:PLA = 1:1

EXAMPLE 5

Bioimaging with Microencapsulated Diatrizoate

Figure 9:
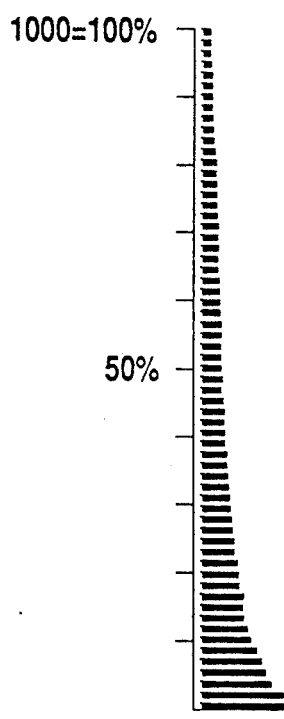
FIG. 9 is a microcapsule size distribution curve prepared from data obtained from Coulter Counter measurements. The mean particle size for the PLA-PHE microcapsules loaded with diatrizoic acid is 3 μm with a range from 2-7 μm.
Figure 10A:
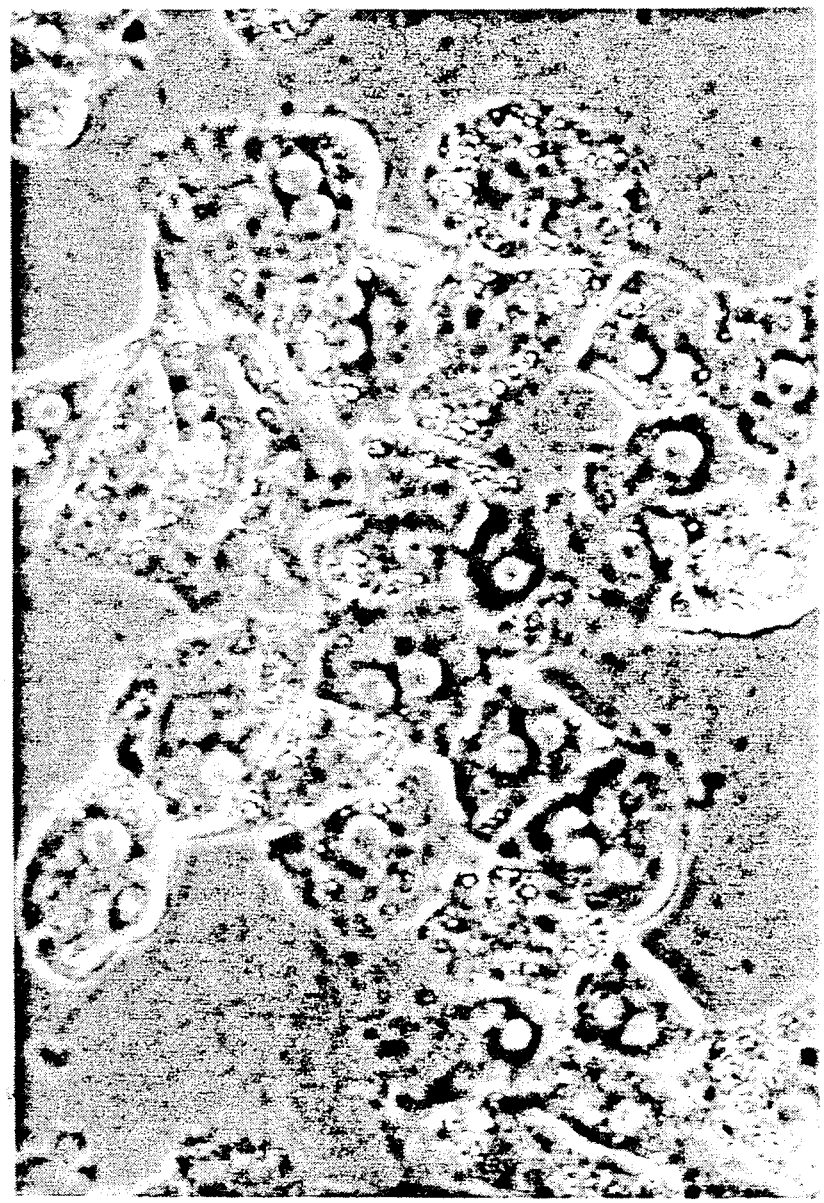
FIG. 10 is a normal mouse hepatocyte culture shown under 40× magnification. All plates were seeded with aliquots from the same cell suspension. 10A shows control (no capsules) hepatocytes; 10B shows hepatocytes incubated for two hours with meglumine diatrizoate-loaded 1 μm polylactide capsules.
FIG. 10C shows hepatocytes incubated for two hours with meglumine diatrizoate-loaded 1 μm phenylalanine ester-conjugated polylactide capsules.
Figure 10B:
Figure 10C:
Figure 11A:
FIG. 11 is a normal mouse Kupffer cell culture shown under 40× magnification. All plates were seeded with aliquots from the same cell suspension. 11A shows control hepatocytes; 11B shows Kupffer cells after incubation for two hours with 1 μm polylactide capsules; 11C shows Kupffer after incubation for two hours with 1 μm phenylalanine ester-conjugated polylactide capsules.
Figure 11B:
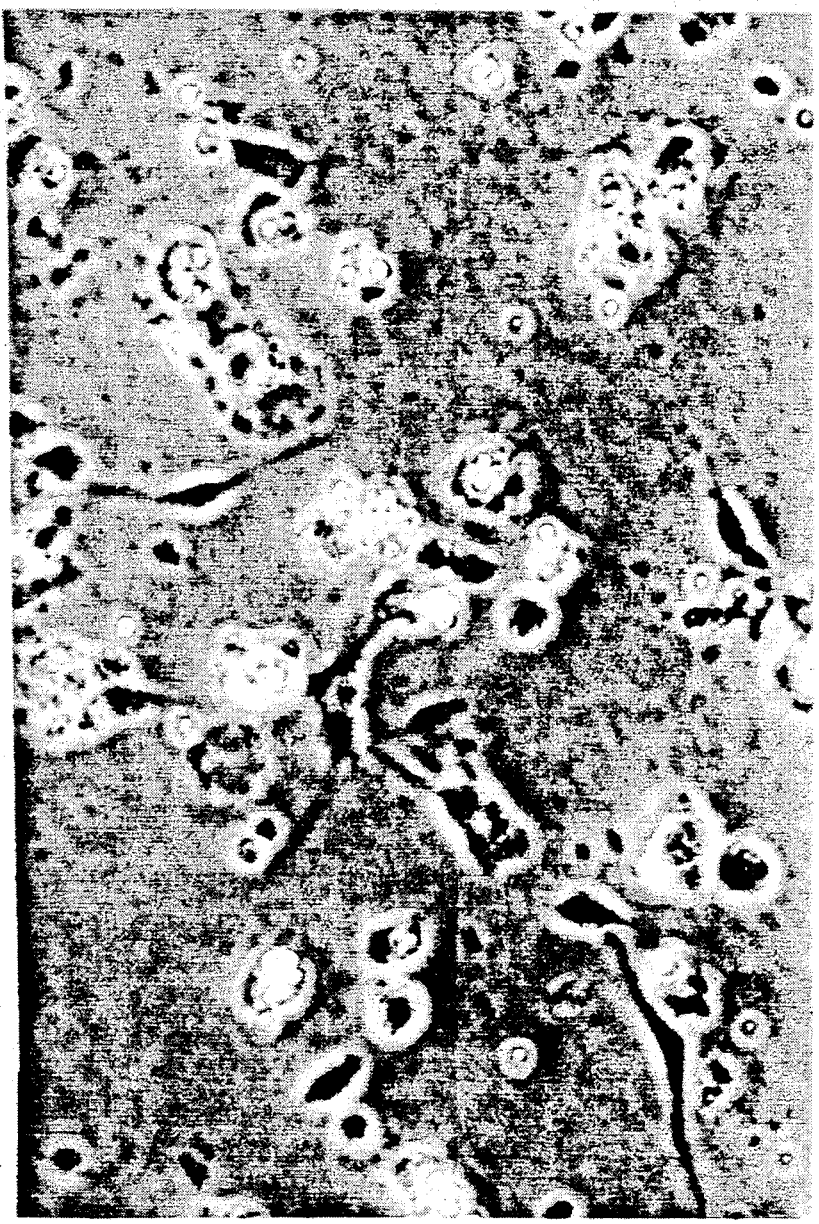
Figure 11C:
Figures 12A, 12G:
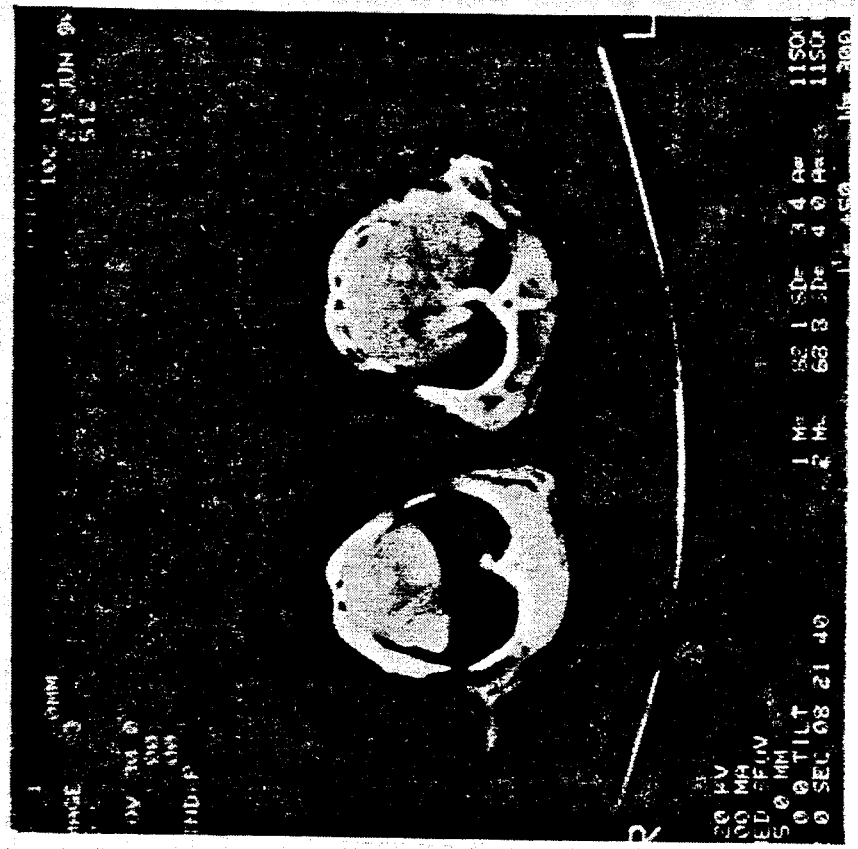
FIG. 12 shows a computerized tomographic images of two rabbits after intravenous injection with microencapsulated meglumine diatrizoate. A-F show distribution of 1 μm polylactide capsules loaded with meglumine diatrizoate before (A) and immediately post-injection (B), 1 hr. (C), 2 hr. (D), 57 hr. (E), and 120 hr. (F). G-L show distribution of the 1 μm phenylalanine-conjugated polylactide capsules loaded with meglumine diatrizoate before (G) and immediately post-injection (H), 1 hr. (I), 2 hr. (J), 57 hr. (K), and 120 hr. (L).
Figures 12B, 12H:
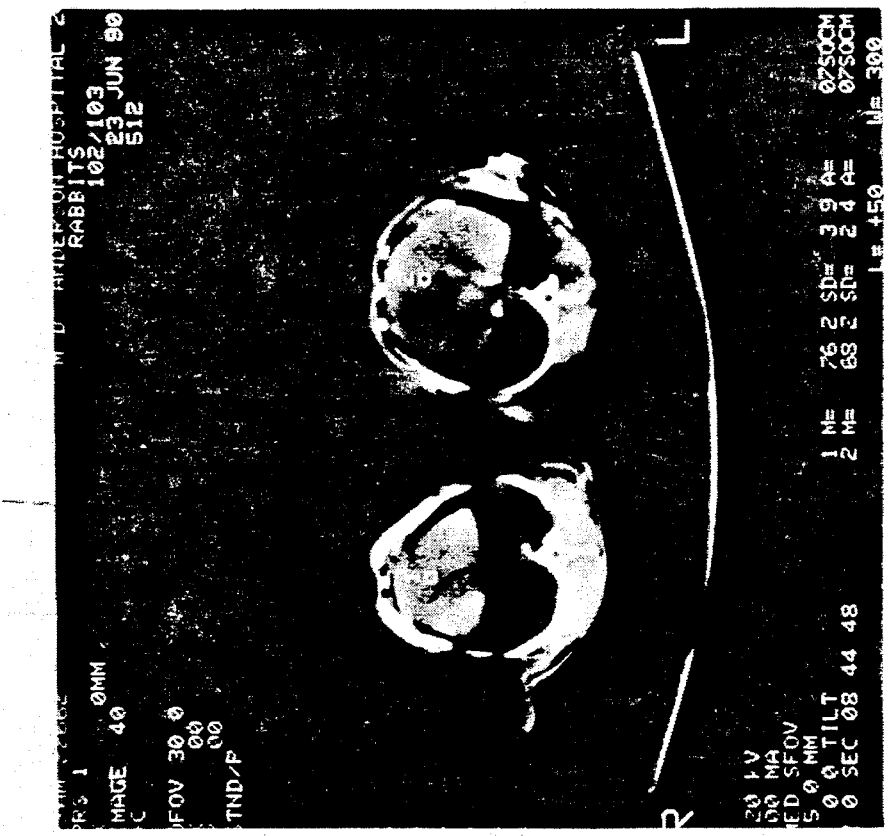
Figures 12C, 12I:
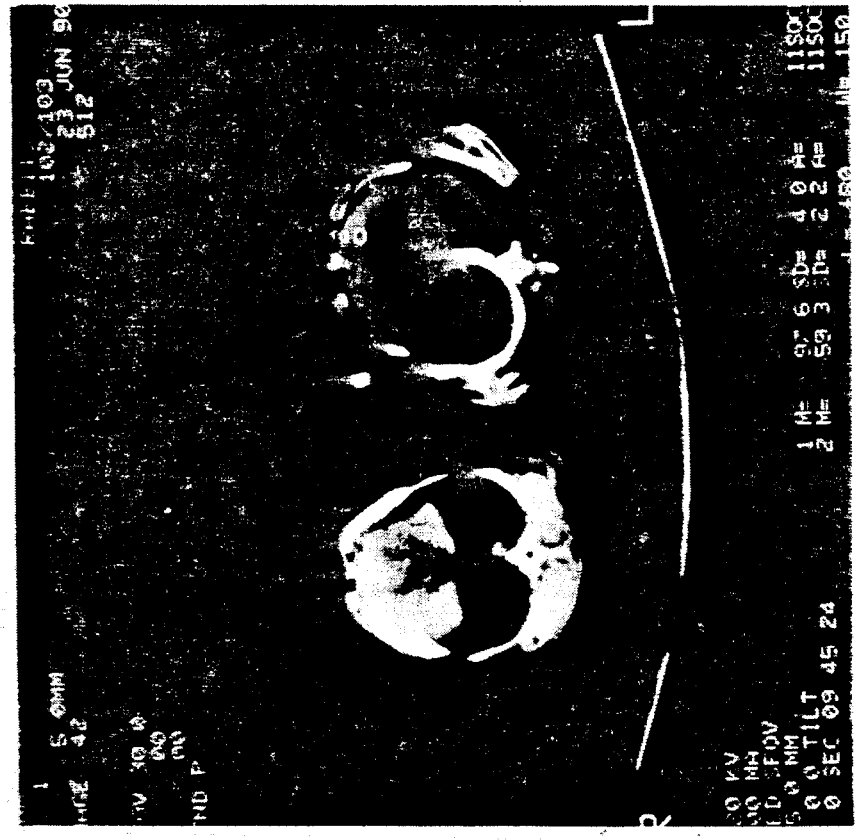
Figures 12D, 12J:
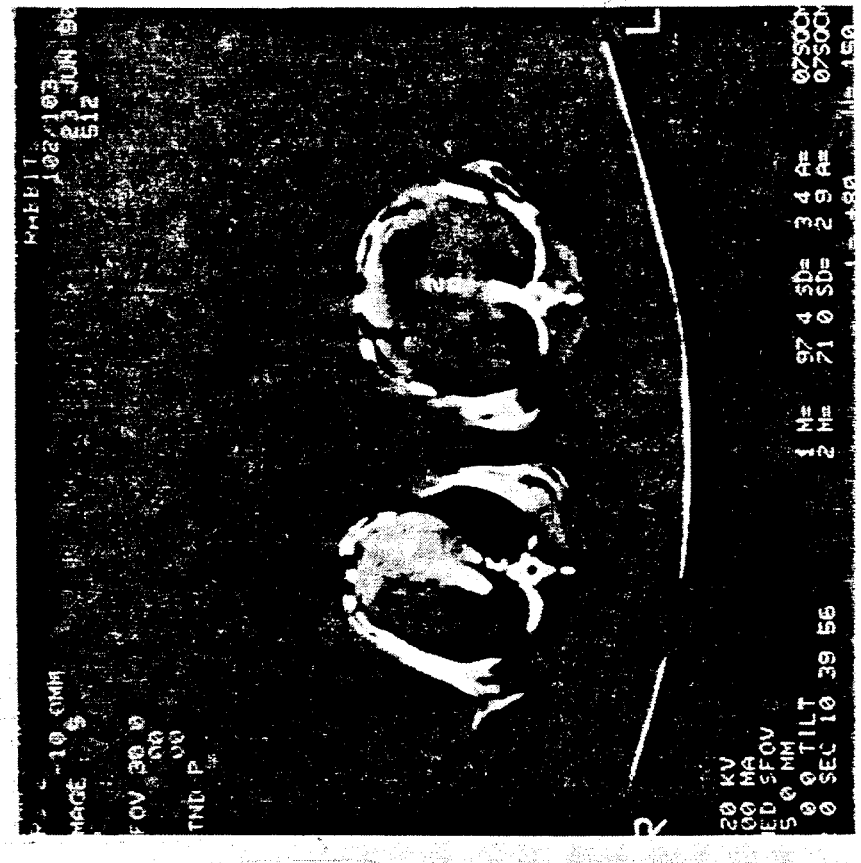
Figures 12E, 12K:
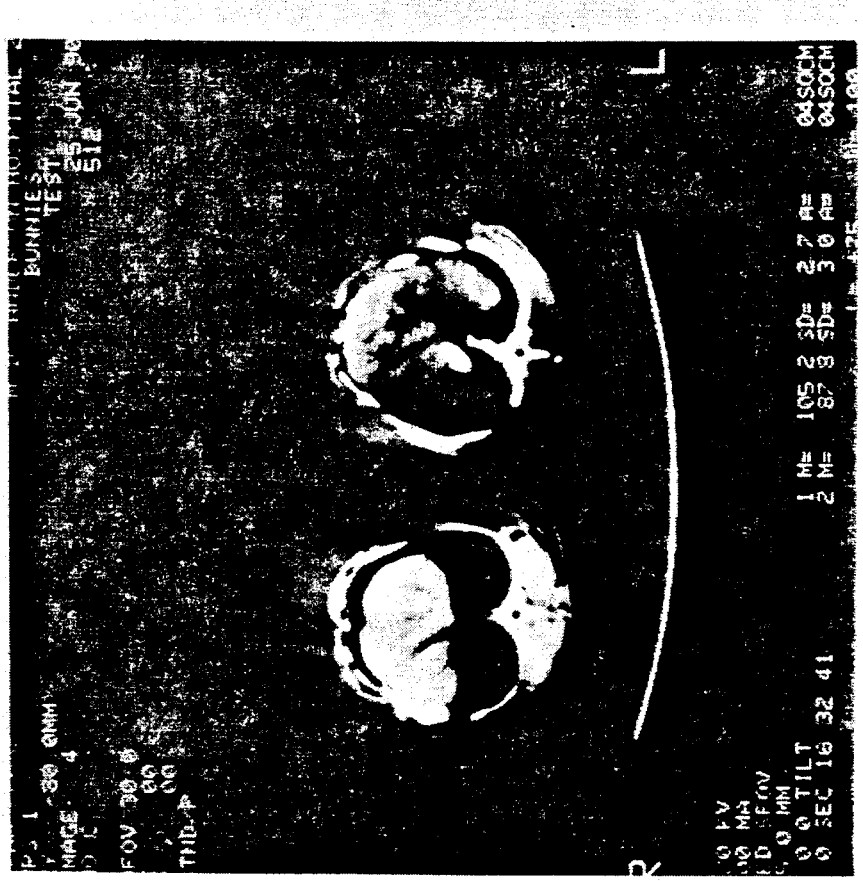
Figures 12F, 12L:
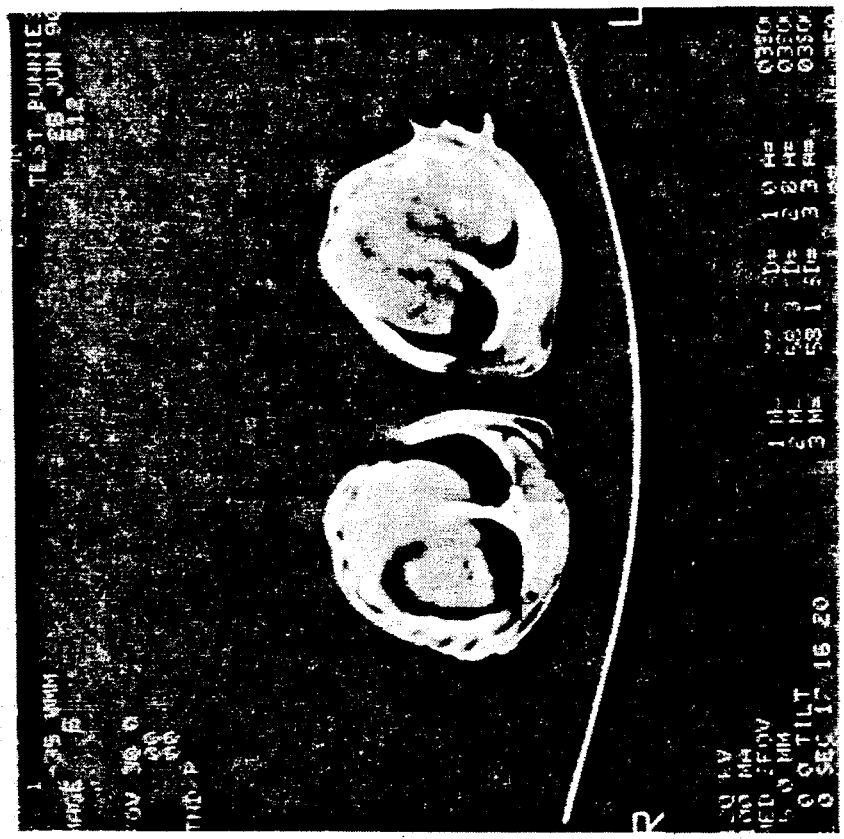

1 μm microcapsules loaded with meglumine diatrizoate were prepared as described in Examples 2 and 3 using PLA and PLA conjugated with phenylalanine (PLA-PHE) as the capsular material. Each preparation was injected intravenously into a rabbit and thereafter monitored by computed tomography for organ uptake. The rabbit receiving PLA-PHE showed a faster liver uptake than the rabbit receiving PLA encapsulated diatrizoate. After 2 hr, the PLA-PHE treated rabbit showed liver uptake and little, if any, contrast in the general circulation while the PLA treated rabbit showed both liver uptake and presence in the general circulation. After 48 and 72 hr, both rabbits showed significant liver uptake. The mean particle size of the PLA-PHE microcapsules loaded with meglumine diatrizoate was determined to be 3 μm, as indicated from a particle size distribution curve obtained using a Coulter Counter, FIG. 9.

EXAMPLE 6

In Vitro Release Rates of 100 μm Microcapsules

Microcapsules were prepared as described in Example 1 using the solvent evaporation method with drug:polymer ratios of 1:1 and 1:3 (w/w) and polyvinyl alcohol as emulsifier. The biodegradable polymers used were PCL, PCLD and PLA. The cytotoxic compounds Tamoxifen and 5-fluorouracil were dissolved in methylene chloride, then added with the emulsifier to a water solution with stirring at 400 rpm. After 6 hr, the capsules were washed with water and air dried. Capsules of approximately 100 μm were collected from mesh screens. Assays on the encapsulated drugs were performed by dissolving 5 mg of the microcapsules in 5 ml methanol. The solution was centrifuged and 100 μl of the supernatant diluted with 3 ml methanol and analyzed spectrophotometrically at 238 nm. A standard solubility time curve was produced using the same procedure by adding 2 mg of both TX and 5-FU. The drug content was calculated as a percent of total capsule weight. Triplicate determinations were made.

Dissolution studies were performed on the microencapsulated drugs. Capped test tubes were filled with 5 ml of 0.05M phosphate buffered saline pH 7.4 and placed in a water bath shaker set at 100 rpm at 37° C. 5 mg of microcapsules were added to each test tube, and sample solutions of 3 ml were collected at different time intervals after centrifugation. After each determination, the sample solutions were returned to each test tube. The concentrations of the drug released from microcapsules were determined by comparison with the standard drug (2 mg) in the same dissolution solution for the controls and measured spectrophotometrically at 238 nm. Determinations were made in triplicate. A Student's t-test (13) was used to compare the sample after 1 hr of incubation and the corresponding sample at different incubation time intervals ($p<0.05$ level).

Figure 5:
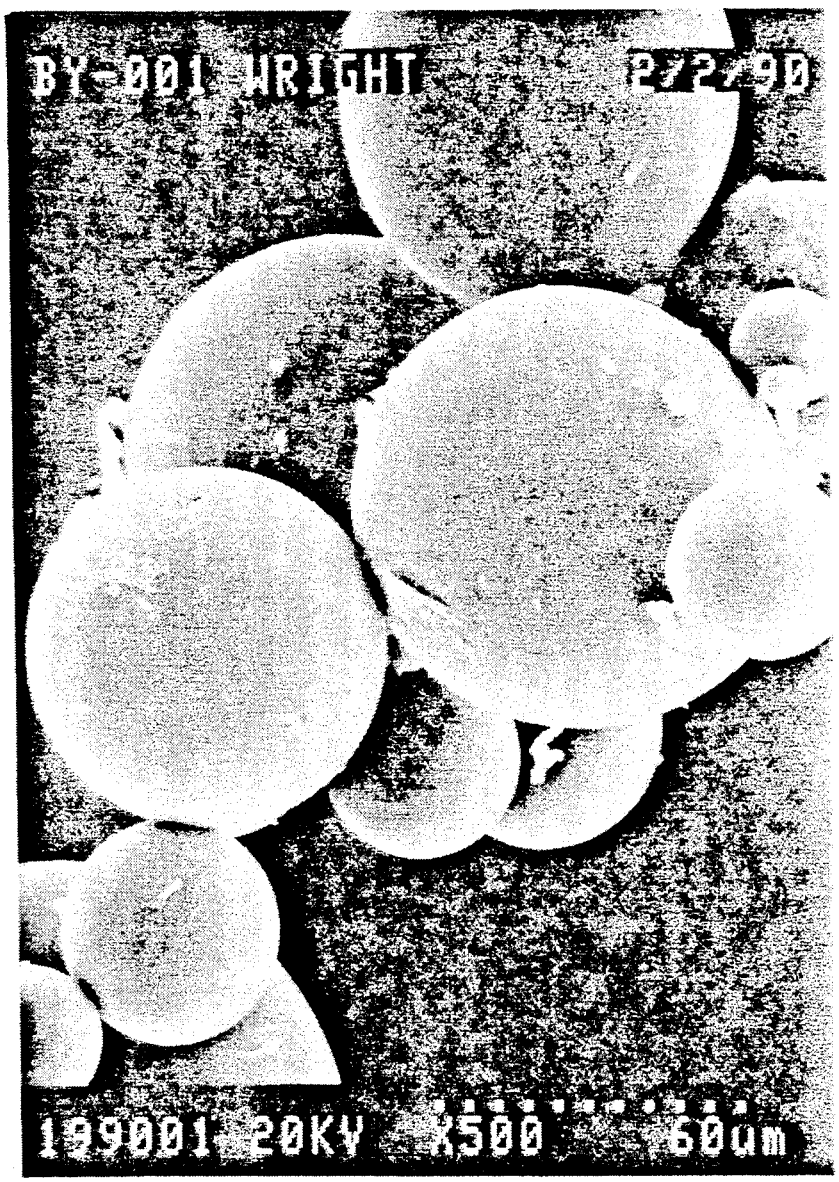
FIG. 5 is a scanning electron micrograph of PLA microcapsules loaded with Tamoxifen with TX:PLA ratios of 1:1.
Figure 6:
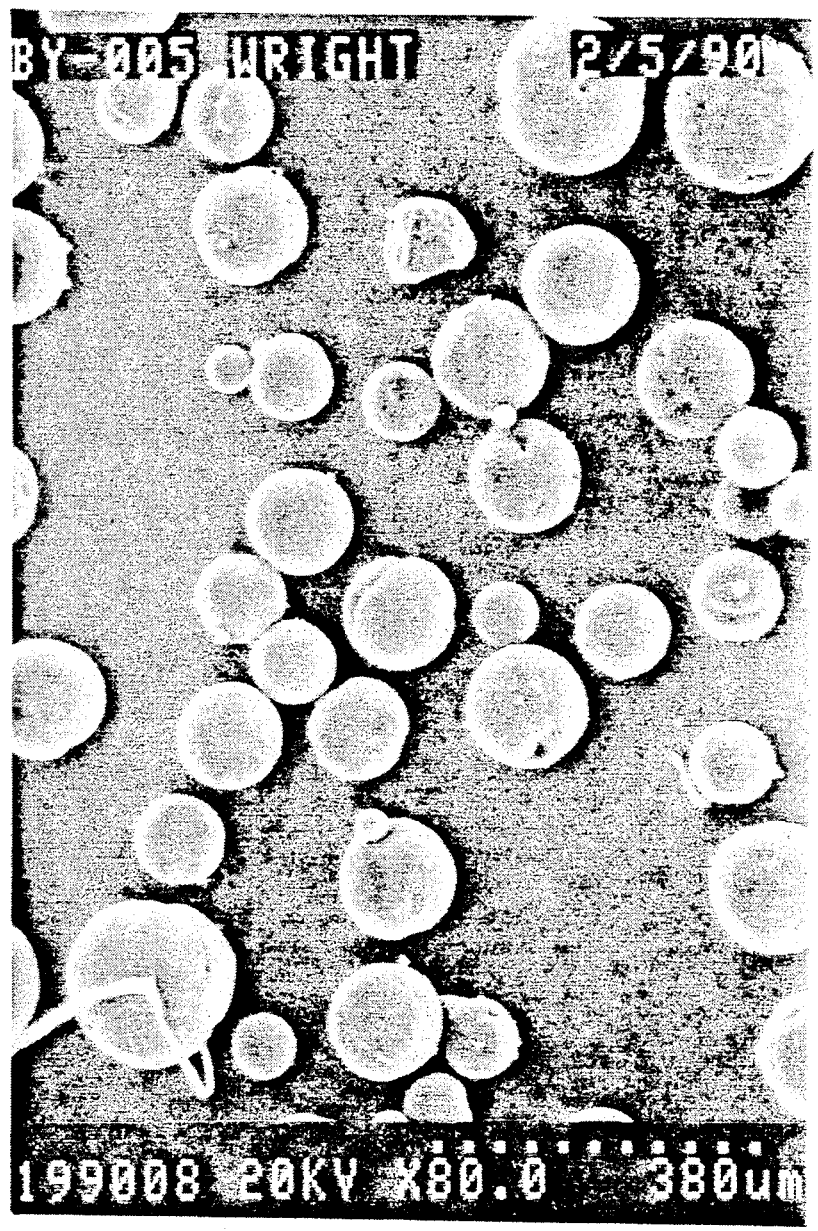
FIG. 6 is a scanning electron micrograph of PCL microcapsules loaded with 5-fluorouracil:PCL ratios of 1:1.

The percent of drug content in the various biodegradable microcapsules is shown in Table 2 below. Scanning electron microscopy showed that all the microcapsules prepared were spherically shaped with smooth outer surfaces (FIGS. 5 and 6).

TABLE 2

| | | % (W/W) DRUG IN MICROCAPSULES | |
|---|---|---|---|
| | | DRUG:POLYMER | |
| DRUG | POLYMER | 1:1 | 1:3 |
| Tamoxifen | PLA | 30.0 | 22.5 |
| | PCL | 30.7 | 13.0 |
| | PCLD | 36.4 | 14.9 |
| 5-fluorouracil | PLA | 8.8 | 8.5 |
| | PCL | 9.9 | 6.6 |
| | PCLD | 7.6 | 7.6 |

Figure 1:
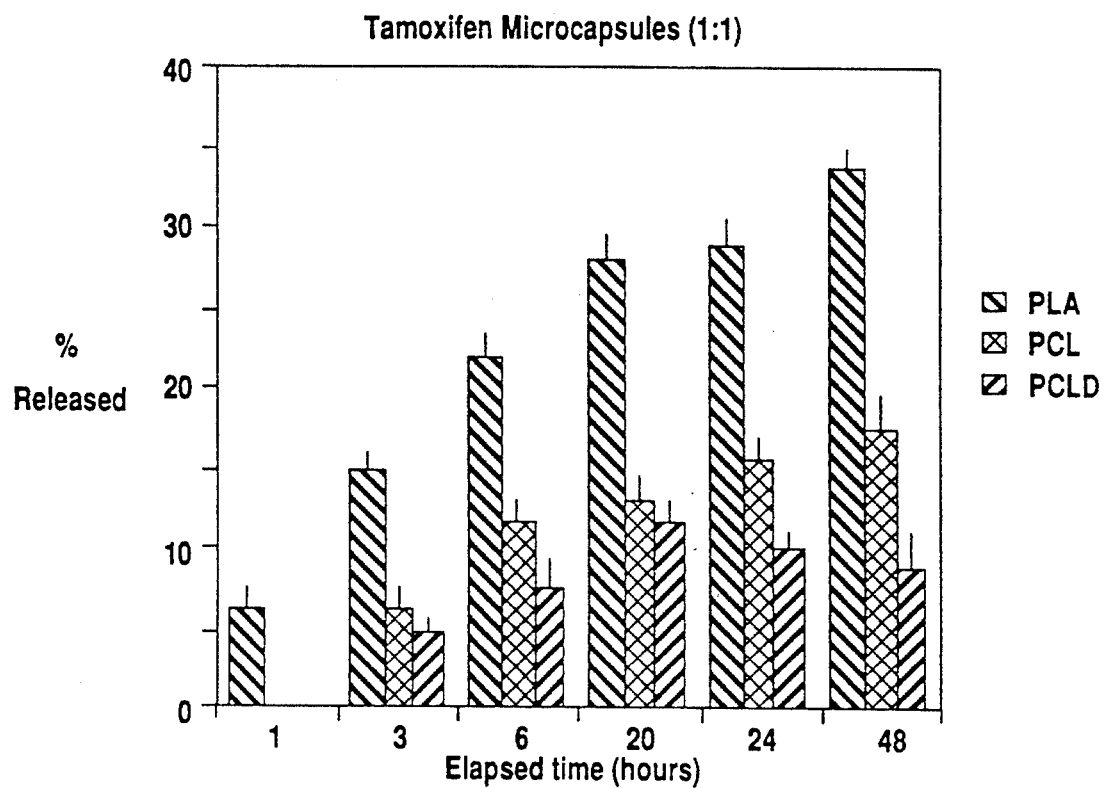
FIG. 1 shows the in vitro profile of Tamoxifen from Tamoxifen microcapsules with Tamoxifen:polymer ratios of 1:1. A statistically significant difference from the corresponding sample after 1 hr of incubation ($p<0.05$ by Student t-test) was determined. Each bar represents the mean ± standard deviation of three samples.
Figure 2:
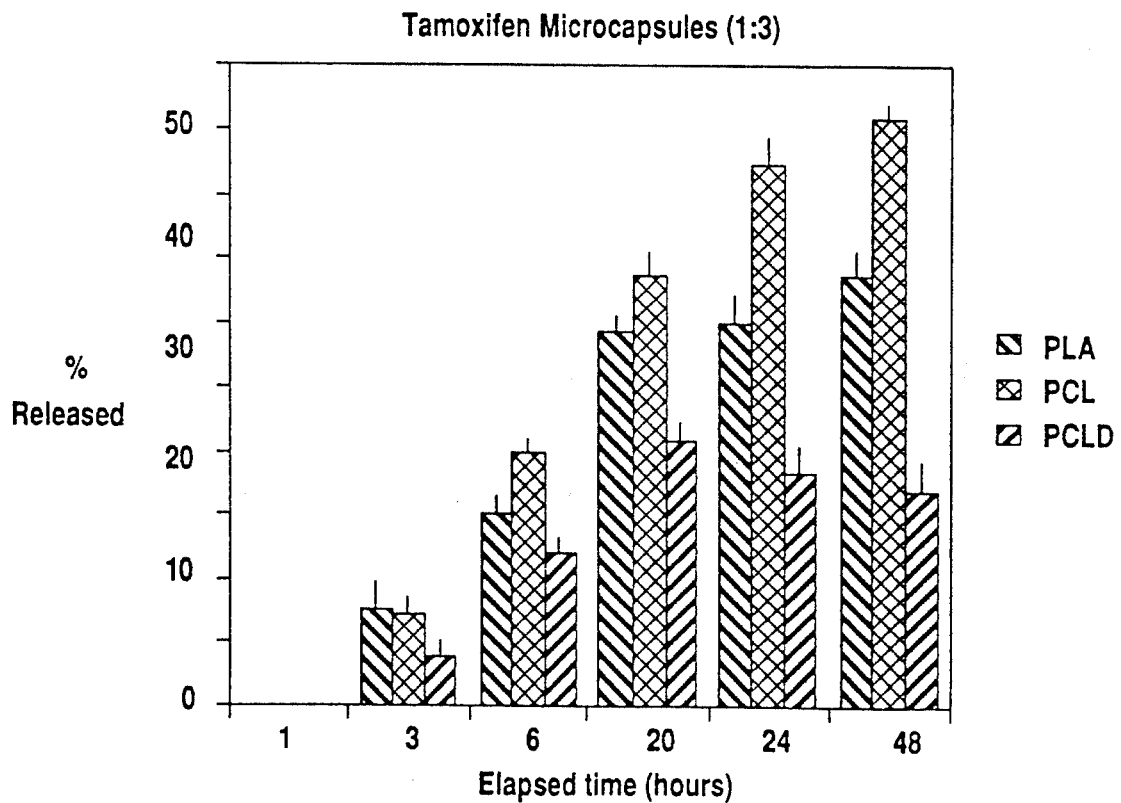
FIG. 2 shows the in vitro release rate profile of Tamoxifen from Tamoxifen microcapsules with Tamoxifen:polymer ratios of 1:3. A statistically significant difference from the corresponding sample after 1 hr of incubation ($p<0.05$, Student t-test) was determined.. Each bar represents the mean ± standard deviation of three examples.
Figure 3:
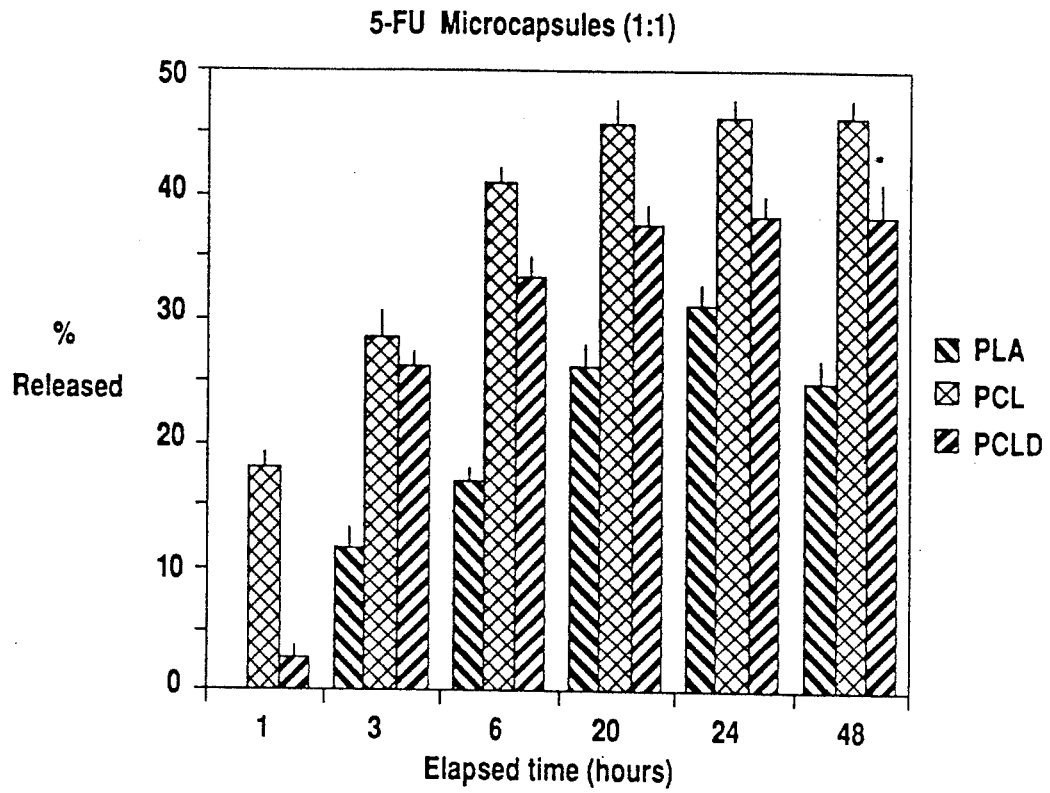
FIG. 3 shows the in vitro release rate profile of 5-fluorouracil from 5-fluorouracil microcapsules with 5-fluorouracil:polymer ratios of 1:1. A statistically significant difference from the corresponding sample after 1 hr of incubation time ($p<0.05$, Student t-test) was determined. Each bar represents the mean ± standard deviation of three samples.
Figure 4:
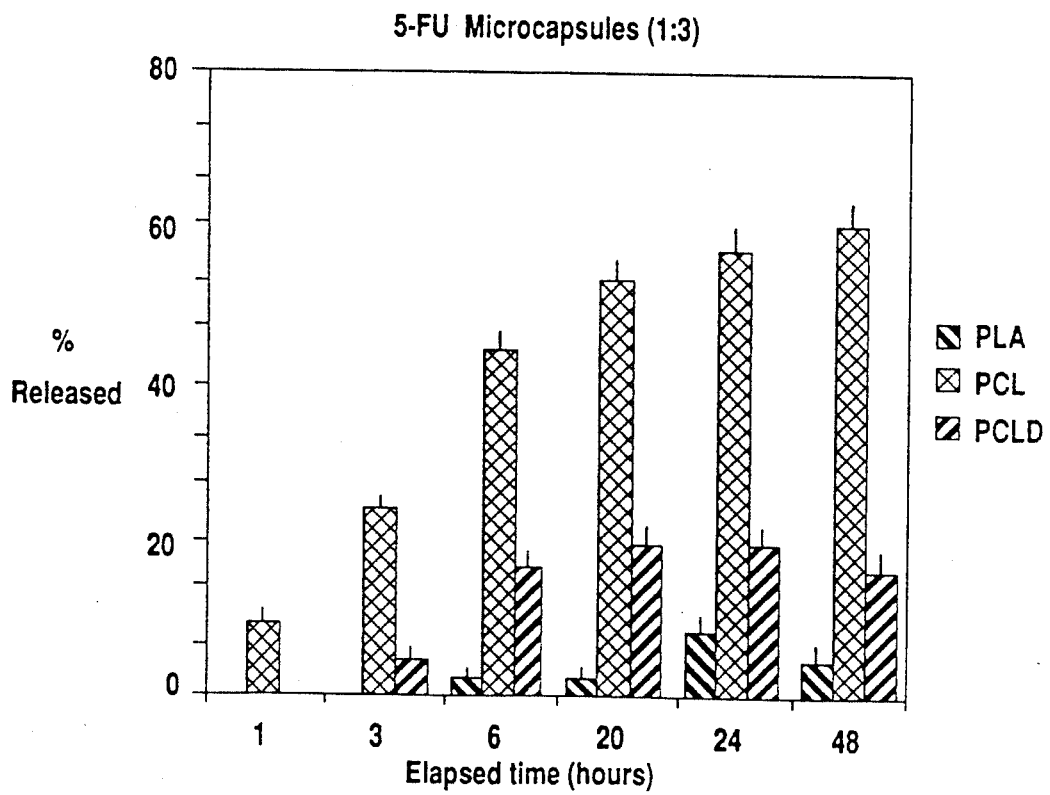
FIG. 4 shows the in vitro release rate profile of 5-fluorouracil microcapsules with 5-fluorouracil ratios of 1:3. A statistically significant difference from the corresponding sample after 1 hr of incubation ($p<0.05$, Student t-test) was determined. Each bar represents the mean ± standard deviation of three samples.

Release rate of TX and 5-FU is shown in FIGS. 1 and 2. The release rate of TX (1:1 ratio) at 48 hr incubation time decreased in the order: PLA>PCL>PCLD; however, the release rate of 5-FU (1:1 and 1:3 ratios) at 48 hr incubation showed PCL>PCLD>PLA. This study indicates that different polymers alter drug release rate.

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, amino acid conjugates to polymers could be employed without affecting the intended nature and practice of the invention. All such modifications are intended to be included within the scope of the claims.

REFERENCES

The references listed below are incorporated herein by reference to the extent they supplement, explain, provide a background for or teach methodology, techniques and/or compositions employed herein.

1. Wright, K. C., Wallace, S., Mosier, B., Mosier, D. J. Microencapsulation 5(1), 13–20 (1988).
2. Wright, K. C., Charnsangavej, C., Wallace, S., Chuang, V. P., Savaraj, N. Cardiovasc. Internat. Radiol. 7, 294–298 (1984).
3. Kawashima, Y., Lin, S. Y., Kasai, A. et al. Drug Dev. Ind. Pharm. USA 10, 467–479 (1984).
4. Benita, S., Benoit, J. P., Puisieur, F. and Thies, C. J. Pharm. Sci. 73, 1721–1724 (1984).
5. Bechtel, W. Radiology 161, 601–604 (1986).
6. Tice et al., EPO 0302582, Feb. 8, 1989.
7. Tice, T. R. and Gilley, R. M. J. Control. Release (Netherlands) 2, 343–352 (1985).
8. Smith, A. and Hunneyball, I. M. Int. J. Pharm. (Netherlands) 30, 215–220 (1986).
9. Mosier, U.S. Pat. No. 4,492,720, Jan. 8, 1985.
10. Jaffe, U.S. Pat. No. 4,272,398, Jun. 9, 1981.
11. Fong, U.S. Pat. No. 4,933,105, Jun. 12, 1990.
12. Bechtel, W., Wright, K. C., Wallace, S., Mosier. B., Mosier, D., Mir, S., Kudo, S. Radiology 161, 601–604 (1986).
13. Bruning, J. L. and Kintz, B. L. "Computational Handbook of Statistics" 2nd Ed., Scott, Foreman and Company, Glenview, Ill. (1977).

Although the present invention has been described in some detail by way of illustration and example for purposes of clarity and understanding, it will be obvious that certain changes and modifications may be practiced within the scope of the claims.

What is claimed is:

1. A method of preparing amino-acid conjugated polymeric microcapsules capable of selective in vivo organ targeting, comprising the steps:

attaching an amino acid to poly-(D,L)-lactic acid to form a modified polymer;

combining water, organic solvent, an emulsifier and the modified polymer to form an emulsion;

agitating the mixture for a period of time sufficient to allow formation of microcapsules of about 0.5 to about 200 μm in size;

removing the organic solvent; and collecting the microcapsules.

2. The method of claim 1 wherein the amino-acid conjugated polymeric microcapsule has a diameter of about 1-5 μm.

3. The method of claim 1 wherein the attached amino acid is tyrosine, tryptophan or methionine.

4. The method of claim 1 wherein the attached amino acid is phenylalanine.

5. The method of claim 1 wherein the amino acid conjugated polymeric microcapsule has a diameter of about 1-3 μm.

6. The method of claim 1 further comprising encapsulating a labeling agent.

7. The method of claim 6 wherein the labeling agent is meglumine diatrizoate.

8. The method of claim 1 further comprising encapsulating a therapeutic agent.

9. The method of claim 8 wherein the therapeutic agent is cisplatin, 5-fluorouracil or Tamoxifen.

10. The method of claim 8 wherein the therapeutic agent is a contrast agent.

11. The method of claim 1 wherein selective in vivo organ targeting is to the liver.

12. The method of claim 6 or 8 further comprising admixing the collected microcapsules with a pharmaceutical carrier suitable for intravascular administration.

13. The method of claim 1 wherein the organic solvent is acetone, ethylene chloride, chloroform, carbon tetrachloride or ethyl acetate.

* * * * *